United States Patent
Nappa

(10) Patent No.: US 11,207,668 B2
(45) Date of Patent: *Dec. 28, 2021

(54) COMPOSITION OBTAINED BY THE SELECTIVE CATALYTIC DEHYDROCHLORINATION OF HYDRCHLOROFLUOROCARBONS

(71) Applicant: THE CHEMOURS COMPANY FC, LLC, Wilmington, DE (US)

(72) Inventor: Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/688,688

(22) Filed: Nov. 19, 2019

(65) Prior Publication Data

US 2020/0086308 A1 Mar. 19, 2020

Related U.S. Application Data

(60) Division of application No. 15/666,770, filed on Aug. 2, 2017, now Pat. No. 10,493,443, which is a continuation of application No. 13/397,956, filed on Feb. 16, 2012, now Pat. No. 9,724,684.

(60) Provisional application No. 61/444,874, filed on Feb. 21, 2011.

(51) Int. Cl.

| C07C 21/18 | (2006.01) |
| C07C 17/25 | (2006.01) |
| B01J 27/12 | (2006.01) |
| B01J 23/26 | (2006.01) |
| B01J 37/26 | (2006.01) |
| B01J 35/10 | (2006.01) |
| B01J 27/132 | (2006.01) |

(52) U.S. Cl.
CPC .......... *B01J 35/1014* (2013.01); *B01J 23/26* (2013.01); *B01J 27/12* (2013.01); *B01J 37/26* (2013.01); *C07C 17/25* (2013.01); *C07C 21/18* (2013.01); *B01J 27/132* (2013.01); *C07C 2527/12* (2013.01)

(58) Field of Classification Search
None
See application file for complete search history.

(56) References Cited

U.S. PATENT DOCUMENTS

| 2,271,356 | A | 1/1942 | Turkevich et al. |
| 3,258,500 | A | 6/1966 | Swamer et al. |
| 4,828,818 | A | 5/1989 | Carlson et al. |
| 5,036,036 | A | 7/1991 | Lerou |
| 6,066,769 | A | 5/2000 | Nappa et al. |
| 7,420,094 | B2 | 9/2008 | Petrov et al. |
| 7,897,823 | B2 | 3/2011 | Miller et al. |
| 7,943,015 | B2 | 5/2011 | Rao et al. |
| 7,982,073 | B2 | 7/2011 | Nappa et al. |
| 7,985,884 | B2 | 7/2011 | Nappa et al. |
| 8,884,082 | B2 | 11/2014 | Sun et al. |
| 2005/0070746 | A1 | 3/2005 | Tung et al. |
| 2008/0058562 | A1* | 3/2008 | Petrov .................. C07C 17/358 570/168 |
| 2009/0030249 | A1 | 1/2009 | Merkel et al. |
| 2009/0043136 | A1 | 2/2009 | Wang et al. |
| 2009/0043137 | A1 | 2/2009 | Wang et al. |
| 2010/0004492 | A1 | 1/2010 | Nappa et al. |
| 2010/0072415 | A1 | 3/2010 | Rao et al. |
| 2010/0076100 | A1* | 3/2010 | Chen ................... B01F 17/0085 521/98 |
| 2010/0249469 | A1 | 9/2010 | Takahashi et al. |
| 2010/0268002 | A1 | 10/2010 | Nose et al. |
| 2010/0312025 | A1 | 12/2010 | Nappa et al. |
| 2011/0031436 | A1 | 2/2011 | Mahler et al. |
| 2011/0112340 | A1 | 5/2011 | Smith et al. |
| 2011/0124930 | A1 | 5/2011 | Smith et al. |
| 2011/0160497 | A1 | 6/2011 | Deur-Bert et al. |
| 2011/0160498 | A1 | 6/2011 | Pigamo et al. |
| 2011/0224466 | A1 | 9/2011 | Sharratt |
| 2011/0313214 | A1 | 12/2011 | Dubois |
| 2012/0215036 | A1 | 8/2012 | Sun et al. |
| 2012/0215037 | A1 | 8/2012 | Sun et al. |
| 2012/0215038 | A1 | 8/2012 | Sun et al. |
| 2014/0031597 | A1* | 1/2014 | Deur-Bert ............. C07C 17/206 570/160 |

FOREIGN PATENT DOCUMENTS

EP 2257512 B1 6/2012

OTHER PUBLICATIONS

Ruthruff, "58. Chromium(III) Oxide Gel" in FERNELIUS ed., "Inorganic Syntheses", vol. II, pp. 190-193, McGraw-Hill Book Co., New York, NY, (1946).

* cited by examiner

*Primary Examiner* — Medhanit W Bahta
(74) *Attorney, Agent, or Firm* — McNees Wallace & Nurick LLC

(57) ABSTRACT

A dehydrochlorination process is disclosed. The process involves contacting $R_fCHClCH_2Cl$ with a chromium oxyfluoride catalyst in a reaction zone to produce a product mixture comprising $R_fCCl=CH_2$, wherein $R_f$ is a perfluorinated alkyl group.

14 Claims, No Drawings

COMPOSITION OBTAINED BY THE SELECTIVE CATALYTIC DEHYDROCHLORINATION OF HYDRCHLOROFLUOROCARBONS

CROSS REFERENCE TO RELATED APPLICATIONS

This application is a divisional application of U.S. application Ser. No. 15/666,770 filed Aug. 2, 2017, which is a continuation application of U.S. application Ser. No. 13/397,956 filed Feb. 16, 2012, which claims benefit of U.S. Provisional Application No. 61/444,874 filed Feb. 21, 2011, the entire contents of which are incorporated herein by reference.

BACKGROUND

Field of the Disclosure

This disclosure relates in general to the selective catalytic dehydrochlorination of hydrochlorofluorocarbons (HCFCs) to make hydrochlorofluoroolefins (HCFOs). More specifically, the catalyst is a chromium oxyfluoride catalyst.

Description of Related Art

Hydrochlorofluoroolefins (HCFOs), having low ozone depletion potential and low global warming potentials, are regarded as candidates for replacing saturated CFCs (chlorofluorocarbons) and HCFCs (hydrochlorofluorocarbons). HCFOs can be employed in a wide range of applications, including their use as refrigerants, solvents, foam expansion agents, cleaning agents, aerosol propellants, dielectrics, fire extinguishants and power cycle working fluids. For example, HCFO-1233xf ($CF_3CCl=CH_2$) can be used as a foam expansion agent, fire extinguishant, refrigerant, et al. HCFO-1233xf is also an intermediate in the production of 2,3,3,3-tetrafluoropropene (HFO-1234yf) which is a refrigerant with zero ozone depletion potential and low global warming potential.

BRIEF SUMMARY OF THE DISCLOSURE

The present disclosure provides a dehydrochlorination process. The process comprises contacting $R_fCHClCH_2Cl$ with a chromium oxyfluoride catalyst in a reaction zone to produce a product mixture comprising $R_fCCl=CH_2$, wherein $R_f$ is a perfluorinated alkyl group.

DETAILED DESCRIPTION

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "dehydrochlorination", as used herein, means a process during which hydrogen and chlorine on adjacent carbons in a molecule are removed.

The term "hydrochlorofluoroolefin", as used herein, means a molecule containing hydrogen, carbon, fluorine, chlorine, and at least one carbon-carbon double bond. Exemplary hydrochlorofluoroolefins in this disclosure include HCFO-1233xf.

The term "alkyl", as used herein, either alone or in compound words such as "perfluorinated alkyl group", includes cyclic or acyclic and straight-chain or branched alkyl groups, such as, methyl, ethyl, n-propyl, i-propyl, or the different isomers thereof.

The term "perfluorinated alkyl group", as used herein, means an alkyl group wherein all hydrogens on carbon atoms have been substituted by fluorines. Examples of a perfluorinated alkyl group include $—CF_3$ and $—CF_2CF_3$.

The term "a chromium oxyfluoride catalyst" is intended to mean a chromium oxyfluoride represented by formula $Cr_2O_xF_y$ wherein $x+y/2=3$.

The term "amorphous" is intended to mean that there is no substantial peak in a X-ray diffraction pattern of the subject solid.

The term "product selectivity to $R_fCCl=CH_2$", as used herein, means the molar percentage of $R_fCCl=CH_2$ obtained in the process compared to the total molar amounts of all products obtained.

The term "dehydrochlorination selectivity to $R_fCCl=CH_2$", as used herein, means the molar percentage of $R_fCCl=CH_2$ based on the total molar amount of $R_fCCl=CH_2$ and $R_fCH=CHCl$ obtained in the dehydrochlorination reaction of $R_fCHClCH_2Cl$.

The term "an elevated temperature", as used herein, means a temperature higher than the room temperature.

Disclosed is a dehydrochlorination process comprising contacting $R_fCHClCH_2Cl$ with a chromium oxyfluoride catalyst in a reaction zone to produce a product mixture comprising $R_fCCl=CH_2$, wherein $R_f$ is a perfluorinated alkyl group.

In some embodiments of this invention, $R_f$ is $-CF_3$ or $-CF_2CF_3$. In some embodiments of this invention, $R_fCHClCH_2Cl$ is $CF_3CHClCH_2Cl$ (HCFC-243db). and $R_fCCl=CH_2$ is $CF_3CCl=CH_2$ (HCFO-1233xf).

Some hydrochlorofluoroolefins of this disclosure, e.g., $CF_3CH=CHCl$ (HCFO-1233zd), exist as different configurational isomers or stereoisomers. When the specific isomer is not designated, the present disclosure is intended to include all single configurational isomers, single stereoisomers, or any combination thereof. For instance, HCFO-1233zd is meant to represent the E-isomer, Z-isomer, or any combination or mixture of both isomers in any ratio.

The starting materials for the dehydrochlorination processes in this disclosure, i.e., $R_fCHClCH_2Cl$, can be synthesized by methods known in the art. For example, HCFC-243db may be prepared by chlorinating $CF_3CH=CH_2$ or by the addition reaction of $CF_2=CHCl$ with $CFClH_2$.

The dehydrochlorination process can be carried out in liquid phase or vapor phase using well-known chemical engineering practice, which includes continuous, semi-continuous or batch operations. The temperature in the reaction zone is typically from about 200° C. to about 500° C. In some embodiments of this invention, the temperature in the reaction zone is from about 275° C. to about 450° C. The dehydrochlorination process can be conducted at superatmospheric, atmospheric, or subatmospheric pressures. The contact time of the starting material $R_fCHClCH_2Cl$ with the catalyst can be largely varied. Typically, the contact time is from about 5 seconds to about 150 seconds. In some embodiments of this invention, the contact time is from about 10 seconds to about 100 seconds.

The contacting step of this invention may be carried out by methods known in the art. In some embodiments of this invention, starting material $R_fCHClCH_2Cl$, optionally with an inert gas and/or HF, is fed to a reactor containing the catalyst. In some embodiments of this invention, starting material $R_fCHClCH_2Cl$, optionally with an inert gas and/or HF, is passed through the catalyst bed in a reactor. In some embodiments of this invention, starting material $R_fCHClCH_2Cl$, optionally together with an inert gas and/or HF, may be mixed with the catalyst in a reactor with stir or agitation.

Optionally, the dehydrochlorination process may be conducted in the presence of HF. In some embodiments of this invention, HF is co-fed into the reactor with the starting material. In some embodiments of this invention, the mole ratio of HF to the starting material $R_fCHClCH_2Cl$ in the reaction zone is from about 0.1:1 to about 50:1. In some embodiments of this invention, the mole ratio of HF to the starting material $R_fCHClCH_2Cl$ in the reaction zone is from about 5:1 to about 25:1. In some embodiments of this invention, the mole ratio of HF to the starting material $R_fCHClCH_2Cl$ in the reaction zone is no more than 0.9. In some embodiments of this invention, the mole ratio of HF to the starting material $R_fCHClCH_2Cl$ in the reaction zone is no more than 0.5. In some embodiments of this invention, the mole ratio of HF to the starting material $R_fCHClCH_2Cl$ in the reaction zone is no more than 0.1.

Optionally, the dehydrochlorination process may also be conducted in the presence of an inert gas such as He, Ar, or $N_2$. In some embodiments of this invention, the inert gas is co-fed into the reactor with the starting material.

It was found through experiments that chromium oxyfluoride catalysts are suitable for selective dehydrochlorination process of this disclosure.

The chromium oxyfluoride catalysts can be made by treating $Cr_2O_3$ with HF, $CCl_3F$, $COF_2$ or hydrofluorocarbons. In one embodiment of this invention, a chromium oxyfluoride catalyst is made by treating dry $Cr_2O_3$ with a fluorination agent such as $CCl_3F$ or HF. This treatment can be accomplished by placing the $Cr_2O_3$ in a suitable container (which can be the reactor to be used to perform the subsequent selective catalytic dehydrochlorination reaction) and thereafter passing HF over the dry $Cr_2O_3$ for a suitable period of time (e.g., about 15 to about 800 minutes) at a suitable temperature (e.g., about 200° C. to about 450° C.) such as what described in Example 1.

In another embodiment of this invention, a chromium oxyfluoride catalyst is made by treating $Cr_2O_3$ with a hydrofluorocarbon at an elevated temperature.

$Cr_2O_3$ is commercially available from BASF Catalysts LLC, 25 Middlesex Essex Turnpike, Iselin, N.J. 08830-0770.

$Cr_2O_3$ can also be prepared by reducing chromium (VI) oxide in water with a suitable reducing agent, such as ethanol, as disclosed in U.S. Pat. No. 3,258,500. Of note is the so-called gel-type activated $Cr_2O_3$ obtained by reducing chromium trioxide ($CrO_3$) and dehydrating the reduced product in the manner disclosed by Ruthruff in "Inorganic Synthesis", Vol. II, pp. 190-193, published in 1946 by McGraw-Hill Book Co., New York, and by Turkevich and Ruthruff in U.S. Pat. No. 2,271,356. In one embodiment of this invention, $Cr_2O_3$ is prepared by dissolving chromium trioxide in water, gradually adding ethanol or other suitable reducing agent to the solution and heating under reflux conditions until the $Cr_2O_3$ gel precipitates, separating the gel from the reaction mixture, drying it, and then dehydrating and activating the product by heating it at a temperature of from about 400° C. to about 600° C. in an inert atmosphere until the water is removed and an anhydrous product is obtained.

$Cr_2O_3$ can also be prepared by pyrolysis of ammonium dichromate (($NH_4)_2Cr_2O_7$) as disclosed in U.S. Pat. No. 5,036,036. Of note is $Cr_2O_3$ prepared by pyrolysing ammonium dichromate and treating (e.g., washing with deionized water) the resulting $Cr_2O_3$ to reduce the alkali metal content to 100 ppm or less. Also of note is $Cr_2O_3$ prepared by first treating ammonium dichromate containing 60-2000 ppm alkali metal to reduce its alkali metal content to less than 60 ppm and then pyrolysing the resulting ammonium dichromate with reduced alkali metal content to form $Cr_2O_3$ containing 100 ppm or less of alkali metal content.

$Cr_2O_3$ can also be prepared by the reaction of chromium (VI) oxide with a reducing solvent, such as methanol, as disclosed in U.S. Pat. No. 4,828,818.

The amount of potassium and other alkali metals in $Cr_2O_3$ can be reduced by a water washing step as disclosed in U.S. Pat. No. 5,036,036. In some embodiments of this invention, the water washing step includes forming a slurry containing 5-15 wt % $Cr_2O_3$ and deionized water. Stirring of this water slurry can be carried out at 35° C. to 65° C. for at least one hour, and in some embodiments for two or more hours. The solids are then recovered by filtration, suitably on a plate and frame filter press. The filter cake can be analyzed for alkali metal content. The washing step can be repeated to obtain a desired level of alkali metal content.

In one embodiment of this invention, the chromium oxyfluoride catalyst has surface area of from about 10 $m^2/g$ to about 800 $m^2/g$.

In another embodiment of this invention, the chromium oxyfluoride catalyst has surface area of from about 20 m²/g to about 400 m²/g.

In another embodiment of this invention, the chromium oxyfluoride catalyst has surface area of from about 40 m²/g to about 300 m²/g.

In one embodiment of this invention, the chromium oxyfluoride catalyst contains an alkali metal content of about 2000 ppm or less.

In another embodiment of this invention, the chromium oxyfluoride catalyst contains an alkali metal content of about 300 ppm or less.

In another embodiment of this invention, the chromium oxyfluoride catalyst contains an alkali metal content of about 100 ppm or less.

In one embodiment of this invention, the chromium oxyfluoride catalyst is amorphous.

In another embodiment of this invention, the chromium oxyfluoride catalyst is prepared from crystalline α-$Cr_2O_3$.

The form of the catalyst is not critical and may be used as pellets, powders or granules.

The effluent from the reaction zone typically includes residual starting materials $R_f$CHClCH$_2$Cl, desired hydrochlorofluoroolefin product $R_f$CCl=CH$_2$, dehydrochlorination byproduct $R_f$CH=CHCl and some other byproducts. The desired product $R_f$CCl=CH$_2$ may be recovered from the product mixture by conventional methods. In some embodiments of this invention, product $R_f$CCl=CH$_2$ may be purified or recovered by distillation.

It was found through experiments that the catalytic dehydrochlorination processes of this disclosure produced desired products with high selectivity. In some embodiments of this invention, the product selectivity to $R_f$CCl=CH$_2$ is at least 90 mole %. In some embodiments of this invention, the product selectivity to $R_f$CCl=CH$_2$ is at least 95 mole %.

It was also found through experiments that the dehydrochlorination reaction of this disclosure is highly selective. The dehydrochlorination reaction of $R_f$CHClCH$_2$Cl may generate both isomers $R_f$CCl=CH$_2$ and $R_f$CH=CHCl. It was found that the dehydrochlorination processes of this disclosure generate substantially more $R_f$CCl=CH$_2$ than $R_f$CH=CHCl. In some embodiments of this invention, the dehydrochlorination selectivity to $R_f$CCl=CH$_2$ is at least 95 mole %. In some embodiments of this invention, the dehydrochlorination selectivity to $R_f$CCl=CH$_2$ is at least 99 mole %.

The reactors, distillation columns, and their associated feed lines, effluent lines, and associated units used in applying the processes of embodiments of this invention may be constructed of materials resistant to corrosion. Typical materials of construction include Teflon™ and glass. Typical materials of construction also include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 demonstrates that contacting HCFC-243db with a chromium oxyfluoride catalyst generates HCFO-1233xf.

Preparation of the Chromium Oxyfluoride Catalyst 6 cc (cubic centimeter) (8.97 gm) of α-chromium oxide were crushed and sieved to 12/20 mesh and filled into an Inconel™ reactor tube (0.43 inch ID) to form a catalyst bed, and were treated with HF according to the following procedure. The α-chromium oxide was heated to 400° C. for two hours under a flow of nitrogen of 37.5 sccm (standard cubic centimeters per minute). At the same flow rate of nitrogen, the temperature was lowered to 300° C. for 80 minutes. While at 300° C., the nitrogen flow was lowered to 26.5 sccm and the HF flow was started at 9 sccm. While maintaining these flows, the temperature was raised to 325° C. for 80 minutes, 350° C. for 80 minutes, 375° C. for 200 minutes, 400° C. for 40 minutes, and 425° C. for 55 minutes. While maintaining the temperature at 425° C., the flow of nitrogen was lowered to 18.8 sccm and the HF raised to 15 sccm for 25 minutes. The flow of nitrogen was then lowered to 11.3 sccm, and the flow of HF was raised to 21 sccm for 30 minutes. The flow of nitrogen was then lowered to 3.8 sccm, and the flow of HF was raised to 27 sccm for 30 minutes. Then nitrogen flow was shut off and the HF flow was raised to 30 sccm for 160 minutes. Afterwards the HF flow was discontinued, and the nitrogen flow was raised to 20 sccm while cooling the reactor tube temperature to ambient.

Dehydrochlorination Reaction

The reactor tube temperature was then raised to the desired temperature, and HCFC-243db was fed into the reactor tube together with $N_2$ and optionally HF as shown in Table 1 below. Products were analyzed by GC-MS and tabulated as mole percentage. The remaining percentages were unknown byproducts.

TABLE

| Temp ° C. | 243db sccm | $N_2$ sccm | HF sccm | CT sec | Conv Mole % 243db 243 | Prod Sel Mole % 1233xf | Prod Sel Mole % 1234yf | Prod Sel Mole % 1233zd | DHC Sel Mole % 1233xf |
|---|---|---|---|---|---|---|---|---|---|
| 297 | 1.82 | 2.34 | 21.55 | 14 | 100% | 95% | 1.9% | 0.9% | 99 |
| 353 | 2.52 | 2.34 | 20.57 | 14 | 100% | 92% | 3.7% | 1.8% | 98 |
| 351 | 2.52 | 2.34 | 20.57 | 14 | 100% | 92% | 3.7% | 1.9% | 98 |
| 348 | 2.1 | 2.34 | 21.19 | 14 | 100% | 92% | 3.7% | 1.8% | 98 |
| 348 | 2.1 | 2.34 | 21.19 | 14 | 100% | 91% | 3.8% | 1.8% | 98 |
| 352 | 1.82 | 2.34 | 21.57 | 14 | 100% | 91% | 4.2% | 1.7% | 98 |
| 346 | 1.82 | 2.34 | 21.57 | 14 | 100% | 91% | 3.8% | 1.6% | 98 |

TABLE-continued

| Temp °C. | 243db sccm | N₂ sccm | HF sccm | C T sec | Conv Mole % 243db 243 | Prod Sel Mole % 1233xf | Prod Sel Mole % 1234yf | Prod Sel Mole % 1233zd | DHC Sel Mole % 1233xf |
|---|---|---|---|---|---|---|---|---|---|
| 398 | 2.52 | 2.14 | 20.58 | 14 | 100% | 88% | 5.7% | 2.9% | 97 |
| 400 | 2.1 | 2.14 | 21.14 | 14 | 100% | 84% | 7.3% | 3.2% | 96 |
| 401 | 2.1 | 2.14 | 21.16 | 14 | 100% | 87% | 6.1% | 2.7% | 97 |
| 397 | 1.82 | 2.14 | 21.50 | 14 | 100% | 87% | 6.3% | 2.3% | 97 |
| 400 | 1.82 | 2.23 | 21.50 | 14 | 100% | 80% | 6.8% | 2.1% | 97 |
| 299 | 2.55 | 2.59 | 0 | 70 | 97% | 92% | 0.9% | 2.1% | 98 |
| 300 | 2.55 | 2.59 | 0 | 70 | 53% | 88% | 0.6% | 2.5% | 97 |
| 302 | 2.1 | 2.49 | 0 | 78 | 61% | 86% | 0.6% | 2.5% | 97 |
| 297 | 2.1 | 2.49 | 0 | 78 | 51% | 84% | 0.6% | 2.6% | 97 |
| 303 | 1.82 | 2.39 | 0 | 85 | 54% | 81% | 0.6% | 2.6% | 97 |
| 302 | 1.82 | 2.39 | 0 | 85 | 50% | 82% | 0.6% | 2.7% | 97 |
| 352 | 2.52 | 2.39 | 0 | 73 | 95% | 78% | 1.4% | 4.2% | 95 |
| 349 | 2.52 | 2.39 | 0 | 73 | 60% | 75% | 1.1% | 4.5% | 94 |
| 350 | 2.1 | 2.39 | 0 | 80 | 78% | 73% | 1.3% | 4.5% | 94 |
| 350 | 2.1 | 2.39 | 0 | 80 | 62% | 71% | 1.3% | 4.8% | 94 |
| 351 | 1.82 | 2.39 | 0 | 85 | 62% | 71% | 1.4% | 4.9% | 94 |
| 348 | 1.82 | 2.39 | 0 | 85 | 55% | 70% | 1.5% | 5.1% | 93 |
| 401 | 2.52 | 2.39 | 0 | 73 | 91% | 62% | 4.4% | 10.5% | 86 |
| 401 | 2.52 | 2.39 | 0 | 73 | 62% | 60% | 4.7% | 12.3% | 83 |
| 401 | 2.1 | 2.39 | 0 | 80 | 78% | 54% | 5.4% | 14.0% | 79 |
| 399 | 2.1 | 2.39 | 0 | 80 | 66% | 54% | 6.4% | 15.8% | 77 |
| 400 | 1.82 | 2.39 | 0 | 85 | 68% | 50% | 7.0% | 16.6% | 75 |
| 397 | 1.82 | 2.29 | 0 | 87 | 60% | 49% | 8.0% | 17.9% | 73 |

Note:
Temp = Temperature; C T = Contact Time; Conv = Conversion; Sel = Selectivity; Prod = Product; DHC = Dehydrochlorination; 243db = HCFC-243db; 1233xf = HCFO-1233xf; 1234yf = HCFO-1234yf; 1233zd = HCFO-1233zd.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A composition comprising:
   a dehydrochlorination catalyst having the formula $Cr_2O_xF_y$, wherein $x+y/2=3$; and
   a product mixture comprising:
   2-chloro-3,3,3-trifluoropropene ranging from 78 mol% to 95 mol%;
   2,3,3,3-tetrafluoropropene ranging from 0.6 mol% to 7.3 mol%; and
   1-chloro-3,3,3-trifluoropropene ranging from 0.9 mol% to 4.2 mol%.

2. The composition according to claim 1 wherein the product mixture is a reaction product stream of a dehydrochlorination reaction.

3. The composition according to claim 1 wherein:
   2-chloro-3,3,3-trifluoropropene is present in an amount ranging from 80 mol% to 95 mol% in the product mixture;
   2,3,3,3-tetrafluoropropene is present in an amount ranging from 1.9 mol% to 6.8 mol% in the product mixture; and
   1-chloro-3,3,3-trifluoropropene is present in an amount ranging from 0.9 mol% to 3.2 mol% in the product mixture.

4. The composition according to claim 3 wherein the product mixture is a reaction product stream of a dehydrochlorination reaction.

5. The composition according to claim 1 wherein:
   2-chloro-3,3,3-trifluoropropene is present in an amount ranging from 91 mol% to 95 mol% in the product mixture;
   2,3,3,3-tetrafluoropropene is present in an amount ranging from 1.9 mol% to 4.2 mol% in the product mixture; and
   1-chloro-3,3,3-trifluoropropene is present in an amount ranging from 0.9 mol% to 1.9 mol% in the product mixture.

6. The composition according to claim 5 wherein the product mixture is a reaction product stream of a dehydrochlorination reaction.

7. The composition according to claim 1 wherein:
   2-chloro-3,3,3-trifluoropropene is present in an amount ranging from 92 mol% to 95 mol% in the product mixture;
   2,3,3,3-tetrafluoropropene is present in an amount ranging from 1.9 mol% to 3.7 mol% in the product mixture; and 1-chloro-3,3,3-trifluoropropene is present in an amount ranging from 0.9 mol% to 1.9 mol% in the product mixture.

8. The composition according to claim 7 wherein the product mixture is a reaction product stream of a dehydrochlorination reaction.

9. The composition according to claim 1 wherein:
2-chloro-3,3,3-trifluoropropene is present in an amount ranging from 84 mol% to 92 mol% in the product mixture;
2,3,3,3-tetrafluoropropene is present in an amount ranging from 3.7 mol% to 6.3 mol% in the product mixture; and
1-chloro-3,3,3-trifluoropropene is present in an amount ranging from 1.6 mol% to 3.2 mol% in the product mixture.

10. The composition according to claim 9 wherein the product mixture is a reaction product stream of a dehydrochlorination reaction.

11. The composition according to claim 1 wherein:
2-chloro-3,3,3-trifluoropropene is present in an amount selected from the group consisting of 78 mol%, 80 mol%, 81 mol%, 82 mol%, 84 mol%, 86 mol%, 87 mol%, 88 mol%, 91 mol%, 92 mol%, and 95 mol%;
2,3,3,3-tetrafluoropropene is present in an amount selected from the group consisting of 0.6 mol%, 0.9 mol%, 1.4 mol%, 1.9 mol%, 3.7 mol%, 3.8 mol%, 4.2 mol%, 5.7 mol%, 6.1 mol%, 6.3 mol%, 6.8 mol%, and 7.3 mol%; and
1-chloro-3,3,3-trifluoropropene is present in an amount selected from the group consisting of 0.9 mol%, 1.6 mol%, 1.7 mol%, 1.8 mol%, 1.9 mol%, 2.1 mol%, 2.3 mol%, 2.5 mol%, 2.6 mol%, 2.7 mol%, 2.9 mol%, and 3.2 mol%;
wherein the composition is a reaction product stream of a dehydrochlorination reaction.

12. The composition of claim 1, wherein HF is additionally present.

13. The composition of claim 1, wherein 1-chloro-3,3,3-trifluoropropene is present in an amount ranging from 2.7 mol% to 3.2 mol% in the product mixture.

14. The composition of claim 1, wherein 1-chloro-3,3,3-trifluoropropene is present in an amount ranging from 2.9 mol% to 3.2 mol% in the product mixture.

* * * * *